United States Patent
Baumgartner et al.

(10) Patent No.: US 7,597,671 B2
(45) Date of Patent: Oct. 6, 2009

(54) LOW-TEMPERATURE REUSABLE THERMOPLASTIC SPLINT

(76) Inventors: Daniel Robert Baumgartner, 11871 Silverdale Way NW. #107, Silverdale, WA (US) 98383; Timothy John Baumgartner, 7701 Rita Rd. NE., Bremerton, WA (US) 98311

( * ) Notice: Subject to any disclaimer, the term of this patent is extended or adjusted under 35 U.S.C. 154(b) by 122 days.

(21) Appl. No.: 11/732,101

(22) Filed: Apr. 3, 2007

(65) Prior Publication Data

US 2008/0249446 A1     Oct. 9, 2008

(51) Int. Cl.
*A61F 5/00* (2006.01)
(52) U.S. Cl. .............................. 602/5; 602/8
(58) Field of Classification Search ........... 602/5–8
See application file for complete search history.

(56) References Cited

U.S. PATENT DOCUMENTS

| | | | |
|---|---|---|---|
| 4,790,300 A | 12/1988 | Marx | |
| 5,016,624 A | 5/1991 | Garrett et al. | |
| 5,632,723 A * | 5/1997 | Grim | 602/19 |
| 5,807,295 A * | 9/1998 | Hutcheon et al. | 602/42 |
| 6,129,695 A * | 10/2000 | Peters et al. | 602/62 |

\* cited by examiner

*Primary Examiner*—Michael A. Brown
(74) *Attorney, Agent, or Firm*—Eric Hanscom; Todd Langford

(57) ABSTRACT

This invention is directed toward a splint, where there is a layer of material, such as fabric-laminated foam neoprene, that encompasses a part of the body intended to be immobilized, supported, or protected, and permanently secured to this layer of material is a low temperature thermoplastic. This thermoplastic is rigid when cool, and malleable when heated. The temperature at which the thermoplastic is malleable is low enough so that the splint can be molded directly on the body. The thermoplastic can be heated, molded, and cooled together with the layer of material. The combined elements of the low temperature thermoplastic with the layer of material create a removable remoldable splint that can be immersed in water without degrading the integrity of the splint.

7 Claims, 9 Drawing Sheets

LOW-TEMPERATURE REUSABLE THERMOPLASTIC SPLINT

CROSS REFERENCE TO RELATED APPLICATIONS

None.

STATEMENT REGARDING FEDERALLY SPONSORED RESEARCH OR DEVELOPMENT

This invention was not federally sponsored.

BACKGROUND OF THE INVENTION

Field of the Invention

This invention relates to orthopedic splints, and more specifically, to a reusable and remoldable splint, which uses low temperature thermoplastic as a rigid support. A key feature of the invention is the method by which the thermoplastic exoskeleton is attached to the neoprene, which allows the split to be made in a variety of durable models in which the thermoplastic component is not easily lost, as in the case where the thermoplastic is an insert in a pocket, or needs to be constantly adjusted, as where the thermoplastic is "loose" and held in place by hook and loop fastener strips or similar means of securement. The wearer of the splint can remove the splint and put it back on whenever he or she decides, without losing the custom fit shape of the splint. Further, the wearer may adjust the size and shape of the splint as treatment progresses, such as when swelling reduces. The splint may be worn in the water since no component of the splint appreciably degrades when immersed in water.

The use of splints dates back to early human history, with significant improvements on the design and implementation of splints beginning within the last few centuries. Splints are used in the healing process of many different ailments, but all with the same main purpose: to immobilize, to some extent, a part of the body.

For a splint to immobilize a part of the body, it needs to be rigid and secured to the body. For optimal immobilization and comfort, the rigid part of the splint should to be molded to that specific body part. Additionally, the ability to temporarily remove the splint whenever the wearer desires without losing its custom fit shape would be beneficial, such as for bathing, cleaning, swimming, or laundering. While a one-time use splint is sufficient, it is more efficient if it can be remolded to immobilize a body party that has, for example, changed in size due to edema or atrophy.

The prior art has several examples of attempts to resolve this problem. Marx, U.S. Pat. No. 4,790,300, discloses a dynamic splint component that has sheets of low temperature thermoplastics that, once molded to the body part, are secured to the body using straps. Attached to these molded sheets of thermoplastic are external supports that are used to limit the range of motion of a joint. The thermoplastic sheets are not used to immobilize the body part, however, but rather are just used as a base in which to attach external supports to limit the range of motion of a joint. These external supports add additional weight to the splint. The supports also make the splint difficult to temporarily remove and put back on whenever the wearer desires.

Garrett et al., U.S. Pat. No. 5,016,624, discloses a reformable support structure that uses low-temperature thermoplastics to create a conformable support structure for an injured arm. This device also relies on an aluminum support structure to maintain the shape, especially while the thermoplastic is cooling. The aluminum support structure is shaped to the arm, and then the thermoplastic conforms to the shape of the aluminum support structure. The additional element of the aluminum support structure makes the splint heavier and more difficult to mold to a specific shape. Further, since the device is a sheet, its application is limited to body parts where a sheet of material can be molded to the body to provide support.

Hutcheon et al., U.S. Pat. No. 5,807,295, discloses a medical bandage material that uses thermoplastic to splint a part of the body. Two layers of material are connected by means of strands, and the space between the two layers contains a low temperature thermoplastic. While the medical bandage can be molded to a part of the body, it is not necessarily remoldable. Additionally, the wearer of the medical bandage cannot temporarily remove the medical bandage whenever the wearer desires.

Thus there has existed a long-felt need for a splint which can be molded to a specific body part, but can also be simply and easily reshaped, reused and refitted as the requirements of the user change. Further, there is a need for a splint that can be worn while submerged in water.

The current invention provides just such a solution by having a splint, where there is a layer of material, such as fabric laminated foam neoprene, that encompasses a part of the body intended to be immobilized, supported, or protected, and permanently secured to this layer of material is a low temperature thermoplastic. This thermoplastic is rigid when cool, and malleable when heated. The temperature at which the thermoplastic is malleable is low enough so that the splint can be molded directly on the body. The thermoplastic can be heated, molded, and cooled together with the layer of material. The combined elements of the low temperature thermoplastic with the layer of material create a removable remoldable splint that can be immersed in water without degrading the integrity of the splint.

Unlike the prior art, the current invention requires no external supports to immobilize the body part. External supports can be cumbersome and add additional weight. Further, additional supports make it more difficult to remove the splint and then put it back on whenever the wearer desires. The current invention solves this problem by using only the low temperature thermoplastic and layer of material to immobilize the desired body part.

Moreover, the current invention can be removed from a body part, and then put back on without losing its custom fit shape. However, the current invention can still be reshaped to fit a body part of a different shape and size by simply reheating the thermoplastic and remolding it to the new body part. This allows for the same splint to be worn at various times by one user.

SUMMARY OF THE INVENTION

The subject invention is a remoldable orthopedic splint. It comprises a layer of material, such as neoprene rubber, that can be attached to a body part. Attached that that layer of material is a low-temperature thermoplastic, which can be heated in various ways, including microwave energy. This thermoplastic is malleable at temperatures low enough that it can be molded directly on a part of the body without causing injury to that part of the body. When this thermoplastic cools, it becomes rigid. The result is a custom fitted splint that will immobilize a part of the body. It can be reheated and remolded as the injury heals, allowing the same splint to be reused after swelling around an injury has reduced. Further, once the injury is healed, the same splint can be used at a later date for another injury.

The layer of material, such as fabricated laminated foam neoprene, should be selected so that it will provide a comfortable fit to the wearer of the splint, and so that circulation is not compromised. The thickness of the material should be selected so that it provides some minimal support, but is flexible and sturdy enough to be easily put on and removed multiple times. The splint's design also allows a user of the invention to place a thermoplastic stay within a compressive sleeve or wrap for a patient to provide support over a specific part of the body. Through this method, the amount of support can be isolated on the wrap or sleeve so that the proper correction is applied to the specific part of the body requiring support, without the necessity of applying splinting pressure to other parts of the body which are not in need of support.

The thermoplastic itself can be secured to the layer of material in various ways. First, the thermoplastic can be secured in a compartment that is attached to the layer of material. This can be done by stitching or otherwise securing an additional layer of material to the base layer of material. The thermoplastic can then be permanently secured inside the compartment by stitching the compartment closed. An additional means of securing the thermoplastic to the base layer of material is by laminating the thermoplastic material, and then sewing the thermoplastic directly to the base layer of material.

The low-temperature thermoplastic can also be bonded to the layer of material. First, a low-temperature thermoplastic panel is cut to the desired size to fit the splint that it will be applied to. Then it is placed on a backing material. The backing material provides both aesthetic and functional value. It hides the thermoplastic and covers any rough edges. Further, the backing material can be chosen to match the color of the rest of the splint, or according to whatever the user desires. Additionally, the exposed side of the backing material can be a Velcro-sensitive material. This allows any straps that the splint may have to adhere to the backing material aiding in securing the splint to the user.

The thermoplastic panel and the backing material are then placed in a heat press and heated, preferably to a temperature of about 280° Fahrenheit for about 30 seconds. The combined heat and pressure make the thermoplastic soft and pliable and adheres it to the backing material, creating a thermoplastic stay. Once this process is complete, the thermoplastic stay is laid flat to cool.

After the thermoplastic stay has cooled, it is once again heated. The thermoplastic stay is placed on the layer of material, such as fabricated laminated foam neoprene, such that the backing material is facing away from the layer of material. The thermoplastic stay is pressed into the layer of material forming a bond, creating the thermoplastic splint. Optionally, the thermoplastic panel can additionally be sewn to the layer of material for a more secure fit.

The resulting thermoplastic splint is then ready for the user. The user can then heat the splint again, typically in a microwave but can also be done with a household iron, making the thermoplastic stay in the splint soft and pliable. This allows the splint to be formed to the user for a custom fit. Once it is molded and cooled, the low-temperature thermoplastic is more rigid than the original flat thermoplastic panel, providing immobilization, support, and protection.

An antibacterial neoprene, such as Antibac neoprene, may be used as the layer of material. Because splints are often worn for extended periods of time, there can be a build up of bacteria between the wearer's skin and the layer of material. An antibacterial neoprene will aid in preventing bacterial growth.

The thermoplastic splint can be used in various ways. The splint could be used for immobilization, a purpose similar to that of a cast. The thermoplastic is formed in a way that wraps the limb circumferentially and does not allow the joint to flex. The invention also offers flexibility above that provided by a cast, as thermoplastic can be modified by heating it and re-molding it to a specific body part, while a cast must be cut away and a new case laid on the injured body part in situations where a cast must be modified.

The splint can be used for support, where the splint would still allow for function of the hand, elbow, ankle, or other body part. The thermoplastic stay would be fitted against the contour of the skin to offer some compression support while still allowing the joint to flex.

The splint can also be used for protection. The affected area, such as a part of the body with a contusion, is protected from impact by the thermoplastic stay that sits above the surface of the affected area. The affected area could be also be padded with additional layers of material between the skin and the thermoplastic stay, providing a protected area with a comfortable fit.

It is a principal object of the invention to provide a splint that can be molded directly on the body part intended to be immobilized, yet when cooled become rigid enough to immobilize the body part.

It is another object of the invention to provide a one piece splint that is simply and easily remoldable, to allow the same splint to be used throughout the progression of treatment, and that such a splint should be comfortable when worn by the user.

It is an additional object of the invention to provide a splint that can be custom fit to a particular body part yet still able to be easily taken off and put back on without losing its custom fit shape.

It should be understood the while the preferred embodiments of the invention are described in some detail herein, the present disclosure is made by way of example only and that variations and changes thereto are possible without departing from the subject matter coming within the scope of the following claims, and a reasonable equivalency thereof, which claims I regard as my invention.

DETAILED DESCRIPTION OF THE FIGURES

Figure 1:
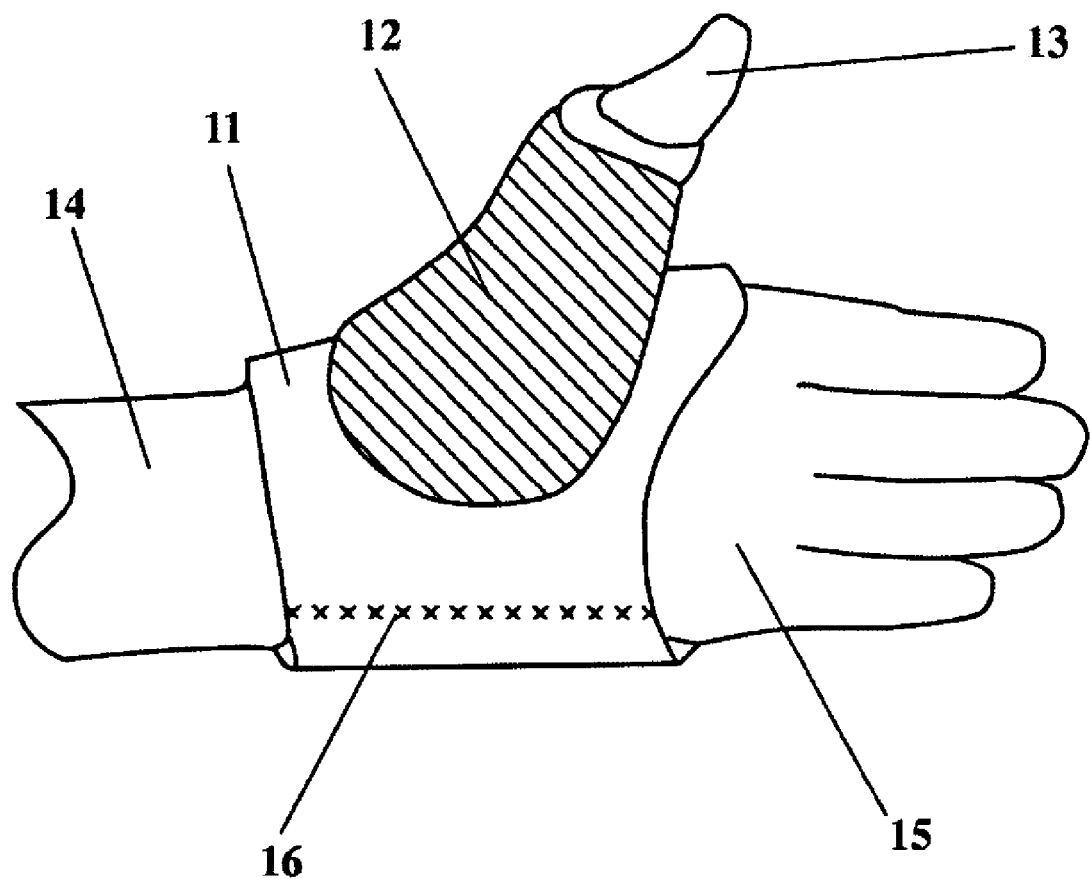
FIG. 1 is a volar view of a thumb stay splint.

FIG. 1 is a volar view of a thumb stay splint. The invention in this iteration comprises a base layer of material 11 that has a low temperature thermoplastic 12 attached to said layer of material 11. Stitching 16 may be used to attach the layer of material 11 to itself to create the shape of the splint. The arm 14 is slid through the layer of material 11 so that the thumb 13 goes through one opening and the fingers 15 go through the other, larger opening.

Figure 2:
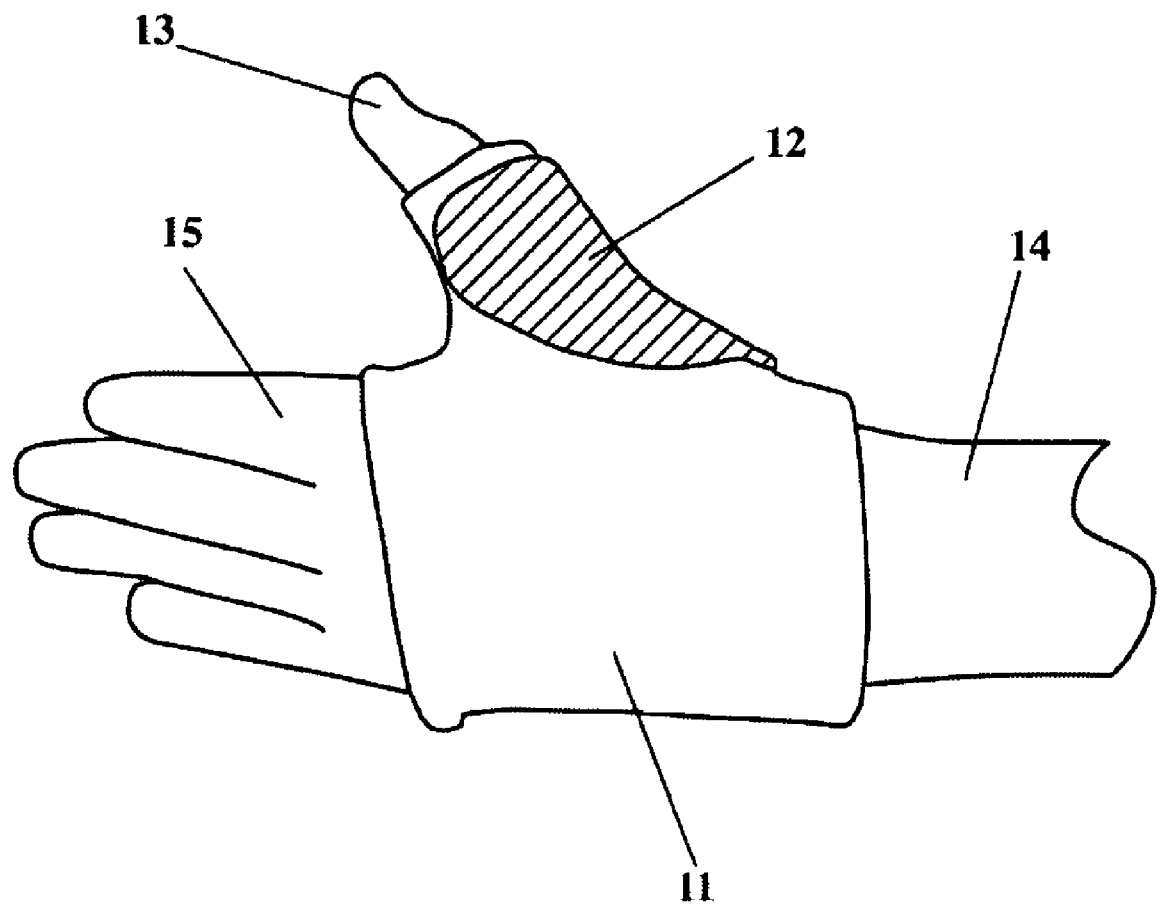
FIG. 2 is a dorsal view of a thumb stay splint.

FIG. 2 is a dorsal view of a thumb stay splint. The invention in this iteration comprises a base layer of material 11 that has a low temperature thermoplastic 12 attached to said layer of material 11. The arm 14 is slid through the layer of material 11 so that the thumb 13 goes through one opening and the fingers 15 go through the other, larger opening.

Figure 3:
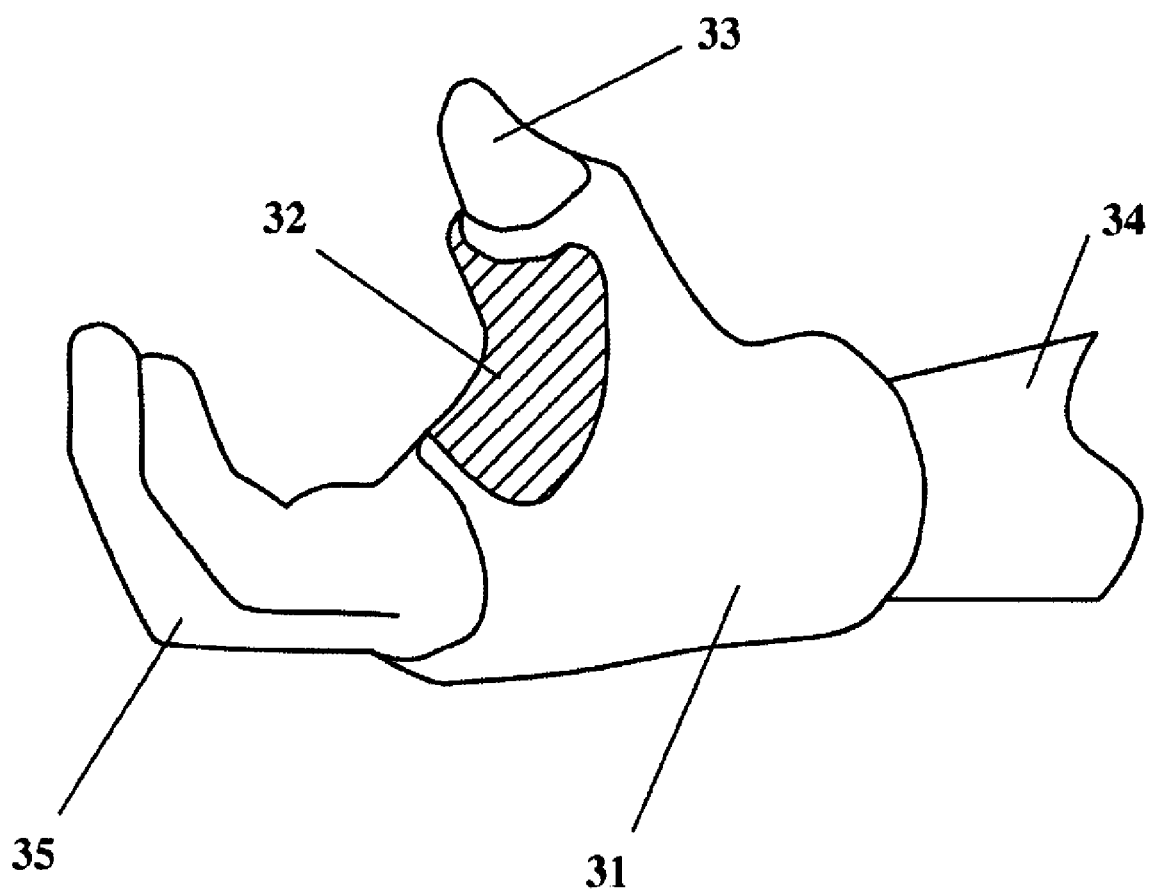
FIG. 3 is a view of a thumb web space splint.

FIG. 3 is a view of a thumb web space splint. The invention in this iteration comprises a base layer of material 31 that has a low temperature thermoplastic 32 attached to said layer of material 31. The arm 34 is slid through the layer of material 31 so that the thumb 33 goes through one opening and the fingers 35 go through the other, larger opening.

Figure 4:
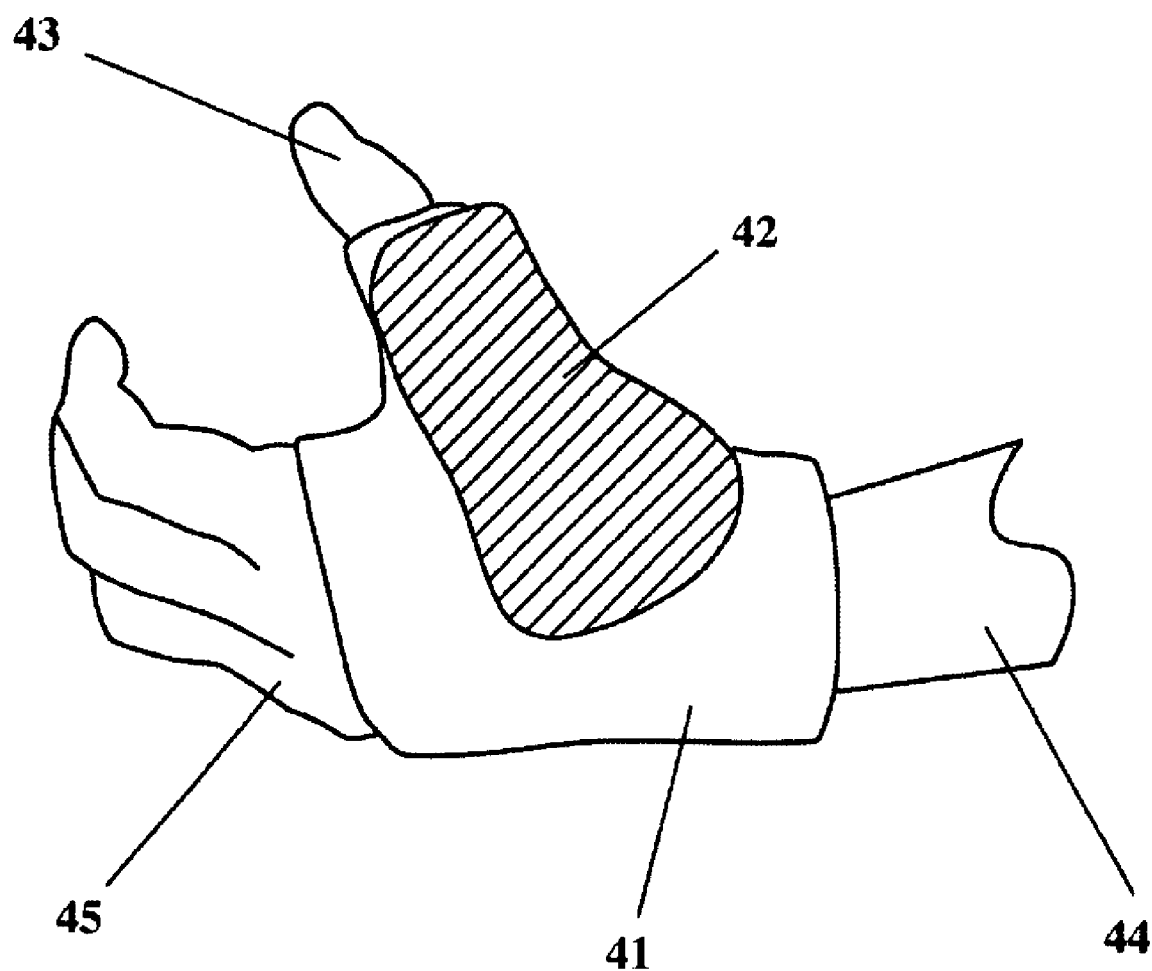
FIG. 4 is a view of a dorsal thumb stay splint.

FIG. 4 is a view of a dorsal thumb stay splint. The invention in this iteration comprises a base layer of material 41 that has a low temperature thermoplastic 42 attached to said layer of material 41. The arm 44 is slid through the layer of material 41 so that the thumb 43 goes through one opening and the fingers 45 go through the other, larger opening.

Figure 5:
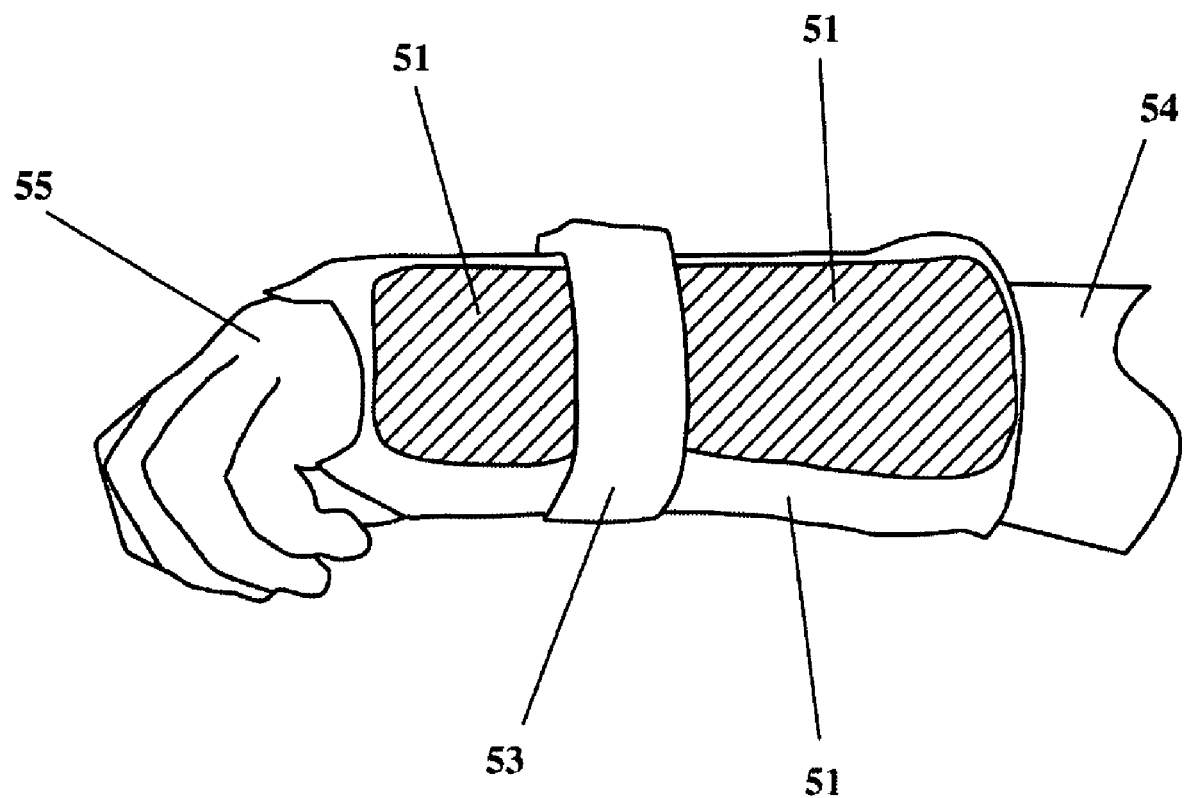
FIG. 5 is a view of an ulnar stay splint.

FIG. 5 is a view of an ulnar stay splint. The invention in this iteration comprises a base layer of material 51 that has a low temperature thermoplastic 52 attached to said layer of material 51. The layer of material 51 is attached the arm 54 by means of a strap 53. The fingers 55 of the arm 54 extend through the end of the layer of material 51 that is secured to the arm 54 by means of a strap 53.

Figure 6:
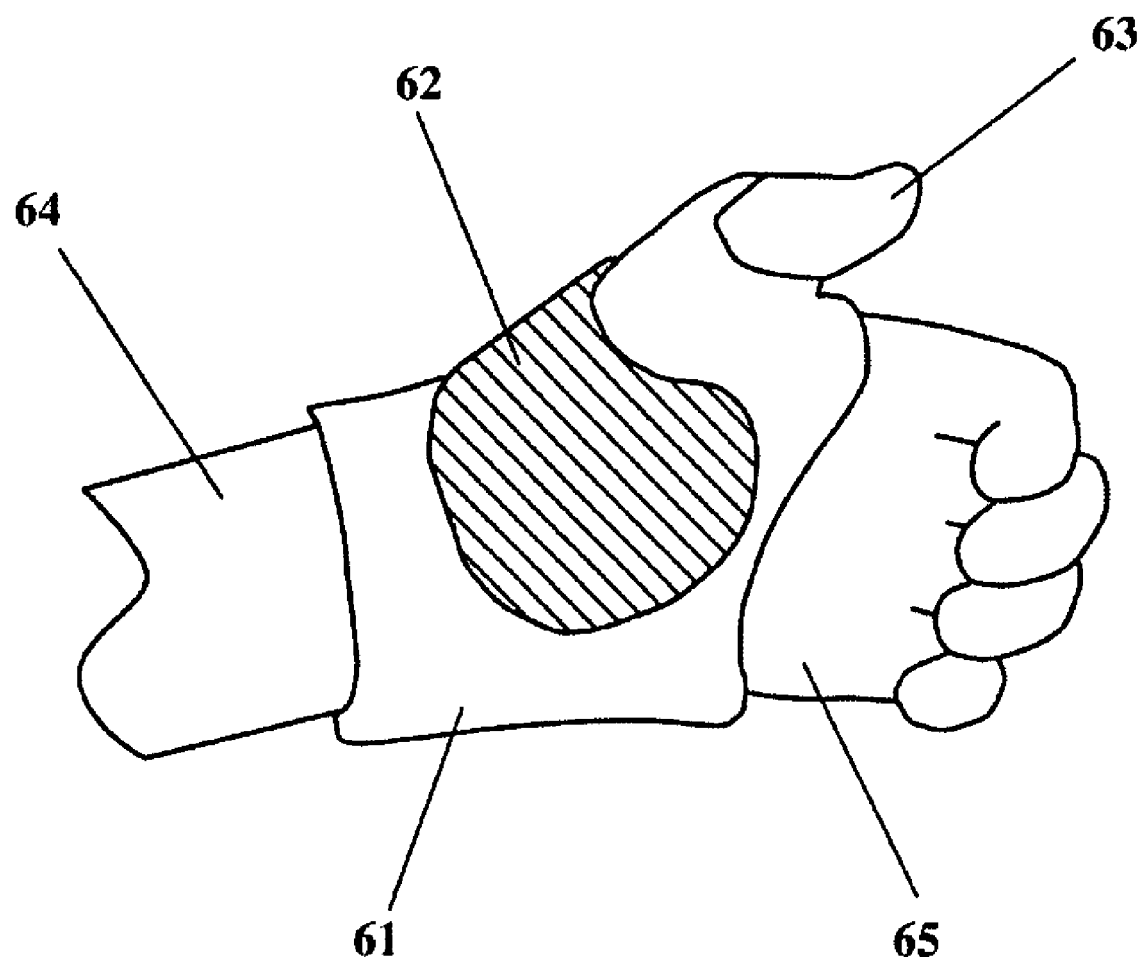
FIG. 6 is a view of a thenar support splint.

FIG. 6 is a view of a thenar support splint. The invention in this iteration comprises a base layer of material 61 that has a low temperature thermoplastic 62 attached to said layer of material 61. The arm 64 is slid through the layer of material 61 so that the thumb 63 goes through one opening and the fingers 65 go through the other, larger opening.

Figure 7:
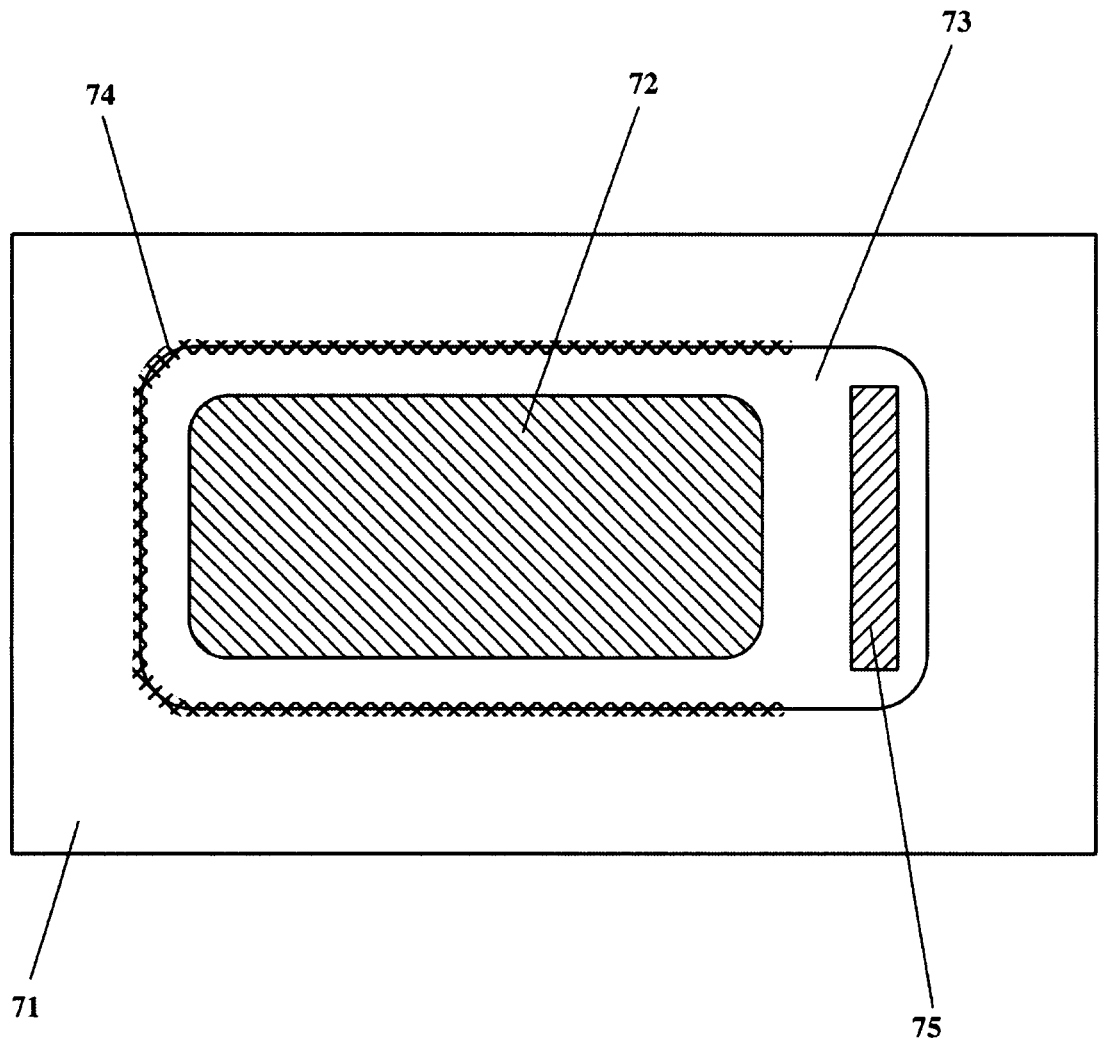
FIG. 7 is a top view of a thermoplastic attached to a layer of material by means of a closable compartment.

FIG. 7 is a top view of a thermoplastic attached to a layer of material by means of a closable compartment. Attached to the base layer of material 71 is a thermoplastic 72. The thermoplastic 72 is placed between the base layer of material 71 and an additional layer of material 73. The additional layer of material 73 is attached to the base layer of material 71 by stitching 74 on three of the four sides of the additional layer of material 73. The remaining side of the additional layer of material 73 is fastened to the base layer of material 71 by means of hook and loop fasteners 75 or the like, creating a closable compartment for the thermoplastic 72 between a base layer of material 71 and an additional layer of material 73.

Figure 8:
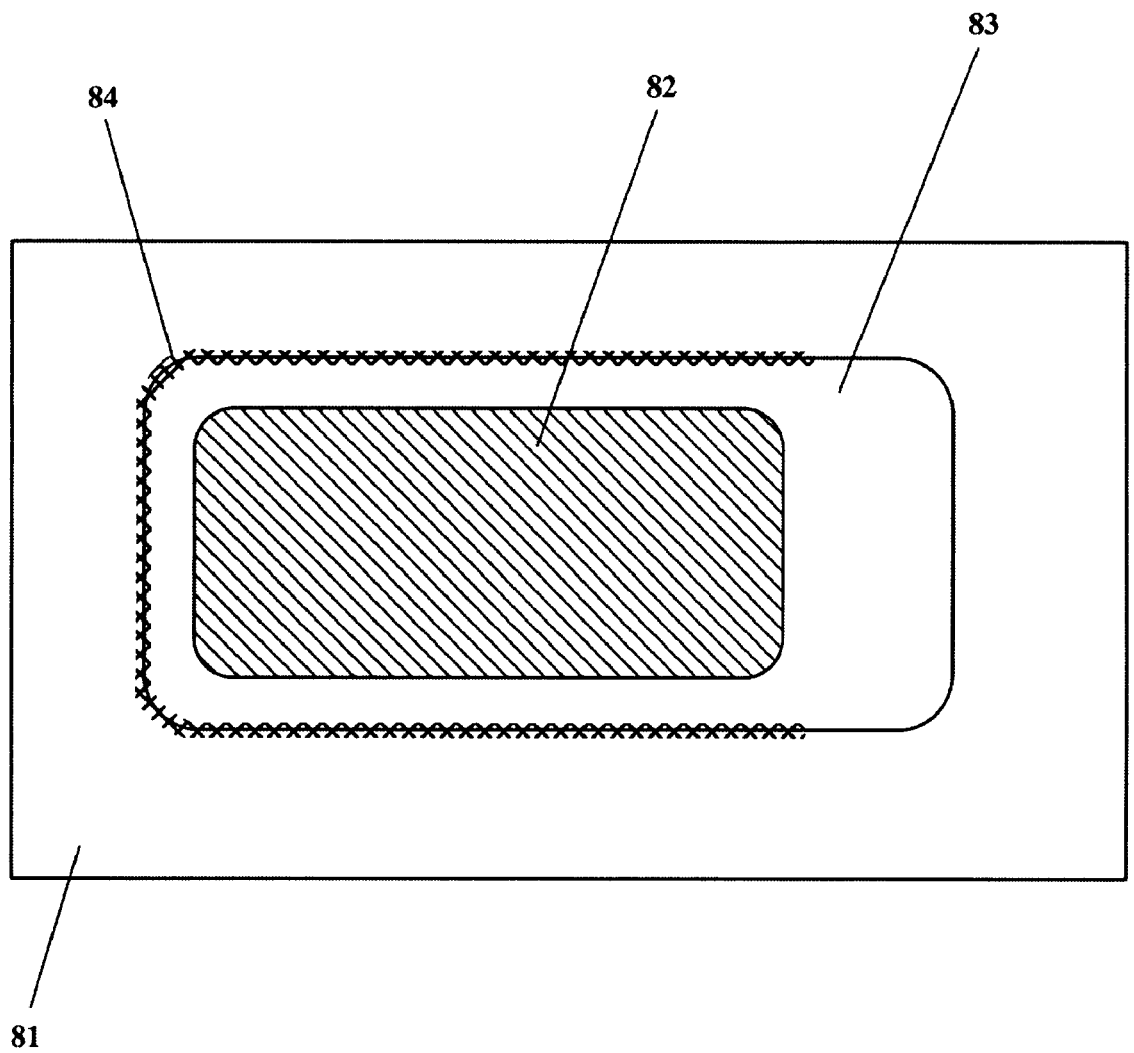
FIG. 8 is a top view of a thermoplastic attached to a layer of material by means of an open compartment.

FIG. 8 is a top view of a thermoplastic attached to a layer of material by means of an open compartment. Attached to the base layer of material 81 is a thermoplastic 82. The thermoplastic 82 is placed between the base layer of material 81 and an additional layer of material 83. The additional layer of material 83 is attached to the base layer of material 81 by stitching 84 on three of the four sides of the additional layer of material 83. The remaining side of the additional layer of material 83 is left unattached to the base layer of material 81 creating an open compartment that retains the thermoplastic 82 between a base layer of material 81 and an additional layer of material 83 by means of friction.

Figure 9:
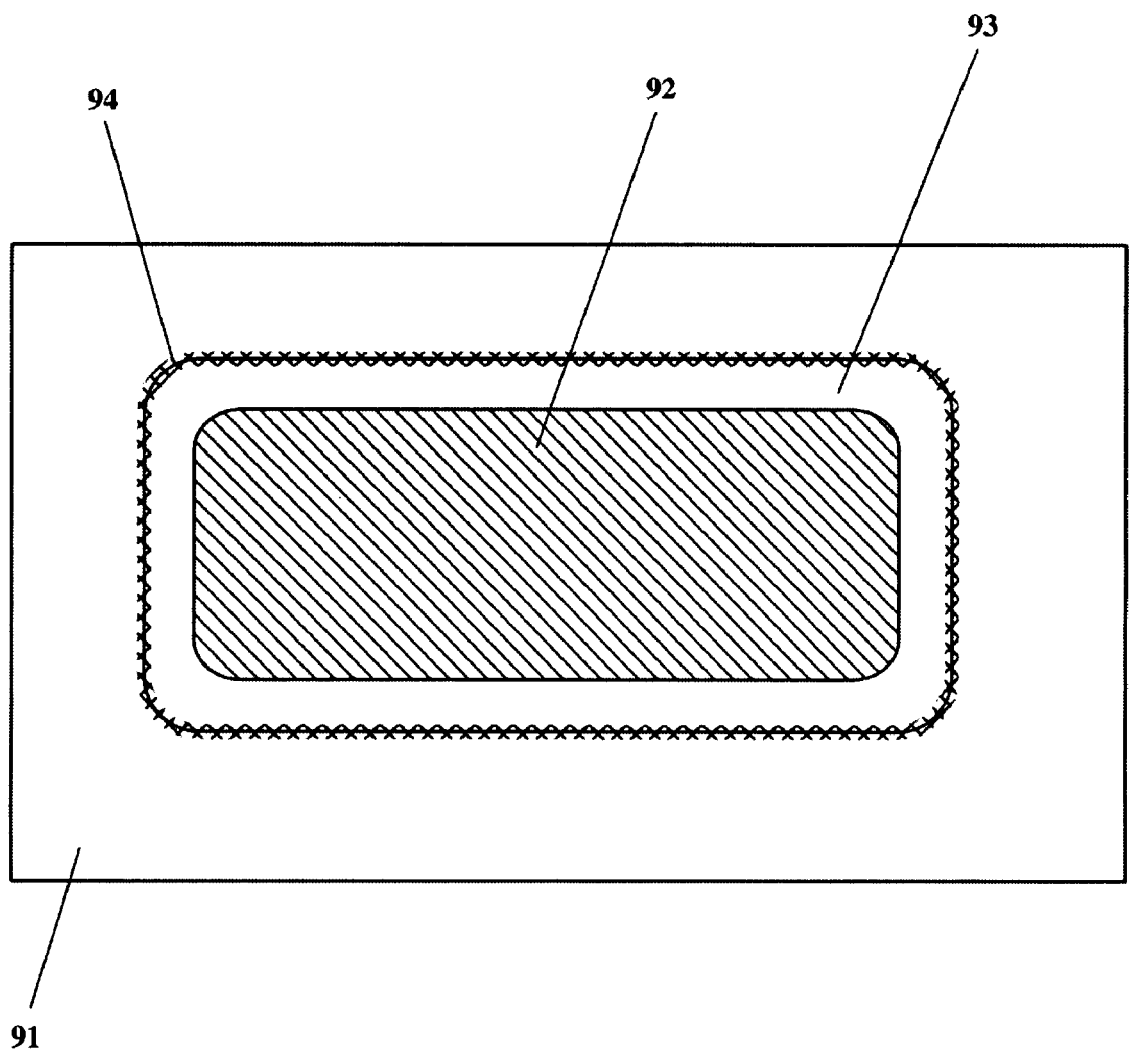
FIG. 9 is a top view of a layer of material with a sealed compartment containing the thermoplastic.

FIG. 9 is a top view of a thermoplastic attached to a layer of material by means of a sealed compartment. Attached to the base layer of material 91 is a thermoplastic 92. The thermoplastic 92 is placed between the base layer of material 91 and an additional layer of material 93. The additional layer of material 93 is attached to the base layer of material 91 by stitching 94 around the periphery of the additional layer of material 93. This creates a sealed compartment that retains the thermoplastic 92 between a base layer of material 91 and an additional layer of material 93.

A thermoplastic splint is created by attaching a low-temperature thermoplastic to a layer of laminated foam neoprene. First, a flat low-temperature thermoplastic panel is cut to a desired size. This thermoplastic panel is then placed against a backing material. The thermoplastic and backing material are then heated together to a temperature of over 250° Fahrenheit for at least 15 seconds, preferably to a temperature of between 275° Fahrenheit and 285° Fahrenheit. The thermoplastic and backing material should then be laid flat and allowed to cool, thereby creating a thermoplastic stay.

The thermoplastic stay should then be secured to a layer of laminated foam neoprene to complete the thermoplastic splint. The thermoplastic stay is heated to a temperature of greater than 140° Fahrenheit and less than 280° Fahrenheit and then placed on the layer of laminated foam neoprene. The backing material of the thermoplastic stay should face away from the layer of laminated foam neoprene. The thermoplastic stay and the layer of laminated foam neoprene are then pressed together thereby forming a bond between the two. For added security, the thermoplastic stay, or panel, can be sewn to the layer of laminated foam neoprene. This creates a thermoplastic splint that is rigid at temperatures below 120° Fahrenheit yet malleable at temperatures above 140° Fahrenheit. This temperature range allows for the splint to be molded directly on a user by heating it to a temperature of 140° and then molding it to the user's body. Once the thermoplastic cools to a temperature of below 120°, it will be rigid and provide support to the user.

What we claim is:

1. A method for attaching a low-temperature thermoplastic to a layer of laminated foam neoprene to create a low-temperature thermoplastic splint, comprising cutting a flat low-temperature thermoplastic panel to a desired size, placing the thermoplastic panel against a backing material and placing these two materials into a heat press and heating the material together to a temperature of over 250° Fahrenheit for at least 15 seconds, then allowing the panel to lay flat and to cool, thereby creating a thermoplastic stay, heating the thermoplastic stay to a temperature greater than 140° Fahrenheit and lower than 280° Fahrenheit and placing the thermoplastic stay on the layer of material laminated foam neoprene with the backing material of the thermoplastic stay facing away from the layer of laminated foam neoprene, then pressing the thermoplastic stay into the layer of laminated foam neoprene thereby forming a bond between the two where the thermoplastic is malleable at temperatures above 140° Fahrenheit and rigid at temperatures below 120° Fahrenheit.

2. The method of claim 1, where the thermoplastic panel and backing material are heated to a temperature of between 275° Fahrenheit and 285° Fahrenheit to create the thermoplastic stay.

3. The method of claim 1, further comprising sewing the thermoplastic panel to the layer of laminated foam neoprene for a more secure fit.

4. The method of claim 1, where the exposed portion of the backing material is made up of either hooks or loops to be used in combination with an opposing hook or loop fastener to aid in securing the thermoplastic splint to a user.

5. A method for using a splint comprising the steps of:
(a) obtaining a splint, where the splint comprises a thermoplastic and a layer of cushioning and insulating material, where the layer of material can be secured to, yet easily attached and removed from, a part of the body intended to be immobilized, where the thermoplastic is permanently secured to the layer of material that, when rigid, helps immobilize the body part intended to be immobilized, where the thermoplastic becomes malleable when heated to a high temperature, where the high temperature is low enough that the splint can be molded directly on the body part intended to be immobilized without burning or otherwise irritating the skin of the body part, and where the thermoplastic becomes rigid when cooled to a low temperature, where the low temperature is high enough so that the thermoplastic does not become malleable during normal use of the splint, and where the thermoplastic can be heated and cooled multiple times and into various shapes;
(b) heating the splint to a temperature of no less than 140° Fahrenheit;
(c) molding the splint directly on a part of the body intended to be immobilized;
(d) allowing the splint to cool; and
(e) securing the splint to the part of the body intended to be immobilized.

6. The method of claim 5, wherein part (b) the splint is heated by a microwave.

7. The method of claim 5, further comprising the steps of:
(f) removing the splint from the part of the body intended to be immobilized,
(g) heating the splint to a temperature of no less than 140°
(h) remolding the splint directly on another part of the body intended to be immobilized;
(i) allowing the splint to cool; and
(j) securing the splint to the other part of the body intended to be immobilized.

* * * * *